United States Patent [19]

Kitada et al.

[11] Patent Number: 5,208,320
[45] Date of Patent: May 4, 1993

[54] POLYPEPTIDE HAVING C-AMP-PRODUCING ACTIVITY

[75] Inventors: Chieko Kitada, Osaka; Takuya Watanabe, Ibaraki, both of Japan

[73] Assignee: Takeda Chemical Industries, Ltd., Osaka, Japan

[21] Appl. No.: 732,059

[22] Filed: Jul. 18, 1991

[30] Foreign Application Priority Data

Jul. 18, 1990 [JP] Japan .................................. 2-187959

[51] Int. Cl.$^5$ ........................ A61K 37/02; C07K 7/10
[52] U.S. Cl. ................................... 530/324; 530/325; 530/326
[58] Field of Search ........................ 530/324, 325, 326; 514/12, 13

[56] References Cited

FOREIGN PATENT DOCUMENTS 404034 6/1990 European Pat. Off. .
404652 6/1990 European Pat. Off. .

OTHER PUBLICATIONS

Ogi et al., *Biochemical and Biophysical Research Communications,* vol. 173, No. 3, 1990.
Nilsson, vol. 60, No. 2, *FEBS Letter,* Dec. 1975.
Kimura et al., Biochemical and Biophysical Research Communications vol. 166, No.1 , 1990.
Miyata, et al., *Biochemical and Biophysical Research Communications,* vol. 164, No. 1, 1989.
Miyata, et al., "Isolation and Characterization of a Novel Ovine Hyopthalamic Polypeptide Which Stimulates Adenylate Cylase in Rat Pituitary Cell Cultures", Proceedings of the 19th Annual Meeting of the Society for Neuroscience, 1989, p. 1277.
A. Miyata, et al., Biochem, Biophys. Res. Commun., 164:567–574 (1989).
C. Kimura, et al. Biochem. Biophys. Res. Commun., 166:81–89 (1990).
K. Koves, et al., Endocrinology, 127:264–271 (1990).

*Primary Examiner*—Merrell C. Cashion, Jr.
*Assistant Examiner*—S. G. Marshall
*Attorney, Agent, or Firm*—David G. Conlin; Gregory D. Williams

[57] ABSTRACT

A polypeptide or a pharmaceutically acceptable salt thereof having c-AMP-producing activity is disclosed, the polypeptide being represented by the following general formula:

X-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Y
(X-SEQ ID NO:2 -Y)

wherein X represents any amino acid residue or an acyl group, and Y represents $NH_2$, OH, Ala-$NH_2$, Ala-OH, Ala-Ala-$NH_2$, Ala-Ala-OH, Ala-Ala-Val-$NH_2$ or Ala-Ala-Val-OH.

13 Claims, 1 Drawing Sheet

FIG.1

POLYPEPTIDE HAVING C-AMP-PRODUCING ACTIVITY

TECHNICAL FIELD

The present invention relates to a novel polypeptide having c-AMP (cyclic adenylate monophosphate)-producing activity and a salt thereof.

BACKGROUND ART

As a new biologically active peptide derived from brain hypothalami, testes or the like, polypeptide PACAP38 consisting of 38 amino acid residues have recently been discovered from sheep and humans. The amino acid sequence of PACAP38 is represented by formula I:

(Formula 1)

His Ser Asp Gly Ile Phe Thr Asp Ser Tyr Ser Arg Tyr Arg Lys Gin Met Ala Val Lys Lys Tyr Leu Ala Ala Val Leu Gly Lys Arg Tyr Lys Gln Arg Val Lys Asn Lys (SEQ ID NO: 1)

PACAP38 enhances the production of intracellular c-AMP in hypophysis cells and the production of c-AMP of astroglia cells, which, in turn, increases the survival time of nerve cells.

This activity of PACAP38 is also observed in PACAP-27-NH$_2$ consisting of 27 amino acid residues on the N-terminal side of the peptide. Since PACAP38 has the DNA sequence corresponding to an amidation processing structure, -Leu$^{27}$ Gly$^{28}$-Lys$^{29}$-Arg$^{30}$-, in the cDNA structure thereof, the above-described activity has previously been confirmed in the synthesized PACAP-27-NH$_2$.

On the other hand, vasoactive intestinal peptide (VIP) is a peptide which is known to exist in the brains as a neurotransmitter or a nerve activator. PACAP-27-NH$_2$ has 68% homology with VIP in amino acid sequence. However, VIP is very weak in c-AMP-producing activity.

SUMMARY OF THE INVENTION

An object of the present invention is to provide a PACAP-like small size peptide which enhances the production of c-AMP as compared with VIP.

The present inventors cut the PACAP38 peptide to produce various peptides and assayed their c-AMP-producing activity to find the smallest structure necessary for activity of PACAP38. As a result, the present inventors discovered that the 23 residues on the N-terminal side of the PACAP38 peptide were the smallest structure necessary for activity expression. When this 23 residue peptide further included 24th to 26th residue(s), the 24 to 26 residue peptides also had activity similar to or higher than that of the above-mentioned 23 residues. Other derivatives in which the N-terminal amino acids were substituted by other amino acids also had similar activity.

The present invention provides a peptide represented by the following general formula, a pharmaceutically acceptable salt thereof, and a method for producing the same:

X-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Y
(X-SEQ ID NO:2 -Y)

wherein X represents any amino acid residue or an acyl group, and Y represents NH$_2$, OH, Ala-NH$_2$, Ala-OH, Ala-Ala-NH$_2$, Ala-Ala-OH, Ala-Ala-Val-NH$_2$ or Ala-Ala-Val-OH.

DISCLOSURE OF INVENTION

In the polypeptides of the present invention, X represents any amino acid residue. -;An aromatic amino acid residue is preferable. Examples of such residues include His, Tyr, Phe and Trp. The polypeptide of which X is His has the same N-terminal portion as that of PACAP38. The polypeptide of which X is an acyl group also has similar effect. The acyl groups are preferably acyl groups derived from carboxylic acids. Carboxylic acid-derived acyl groups each having 1 to 8 carbon atoms are preferable. Examples thereof include a formyl group, an acetyl group, a propionyl group, hexanoyl group and benzoyl group. The C-terminus may be either —NH$_2$ or —OH. In general, however, —NH$_2$ gives higher biological activity than —OH.

The pharmaceutically acceptable salts include organic acid salts such as carbonates, acetates, citrates, tartarates and maleate, and inorganic acid salts such as hydrochlorides and sulfates.

Figure 1:
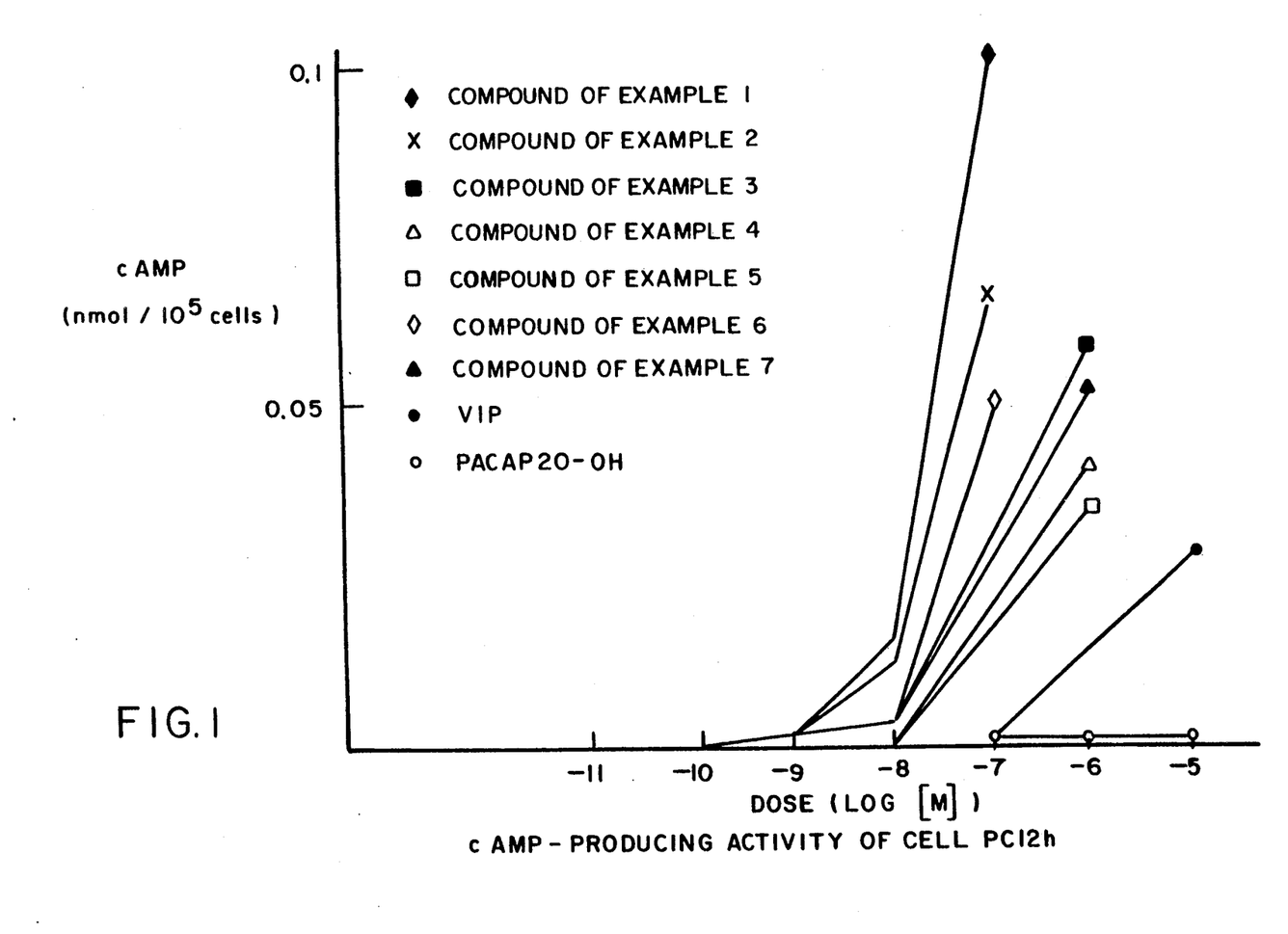
FIG. 1 is a graph comparatively showing c-AMP-producing activity of compounds of the present invention, VIP and PACAP20-OH.

In the present invention, c-AMP producing activity was assayed by determining the amount of c-AMP secreted out of cells with a radioimmunoassay kit for measuring c-AMP, using subcultured cell PC12h of rat adrenal medulla origin. The results revealed that the 23 residues on the N-terminal side of the PACAP peptide is the smallest structure necessary for activity expression, as shown in FIG. 1.

When amino acids and so on are indicated by abbreviations in this specification, the abbreviations adopted are those of the IUPAC-IUB Commission on Biochemical Nomenclature or those commonly used in the art. Examples thereof are as follows. When an optical isomer is capable of existing with respect to the amino acid, the L-form is understood to be represented unless otherwise specified.

PAM : Phenylacetamidomethyl
BHA : Benzhydrylamine
Boc : t-Butyloxycarbonyl
Z : Benzyloxycarbonyl
Cl-Z : 2-Chloro-benzyloxycarbonyl
Cl$_2$-Bzl : 2,6-Dichlorobenzyl
Br-Z : 2-Bromo-benzyloxycarbonyl
Bu : t-Butyl
OBu : t-Butyl ester
OBzl : Benzyl ester
OcHex : Cyclohexyl ester
Mtr : 4-Methoxy-2,3,6-trimethylbenzenesulfonyl
Tos : p-Toluenesulfonyl
Mts : 2,4,6-Trimethylbenzenesulfonyl
NO$_2$: Nitro
DNP : 2,4-Dinitrophenyl
Bom : Benzyloxymethyl
Fmoc : 9-Fluorenylmethyloxycarbonyl
Trt : Trityl
Bum : t-Butoxymethyl
HOBt : 1-Hydroxy benzotriazole
DCC : N,N'-Dicyclohexylcarbodiimide
Gly : Glycine Ala : Alanine
Val : Valine
Leu : Leucine
Ile : Isoleucine
Ser : Serine
Thr : Threonine
Cys : Cysteine
Met : Methionine
Glu : Glutamic acid
Asp : Aspartic acid
Lys : Lysine
Arg : Arginine
His : Histidine
Phe : Phenylalanine
Tyr : Tyrosine
Trp : Tryptophan
Pro : Proline
Asn : Asparagine
Gln : Glutamine The various peptides of the present invention can be produced by conventional methods for peptide synthesis, which may be either solid phase synthesis methods or liquid phase synthesis methods.

For example, when the PACAP peptides of the present invention or the partial peptides thereof are synthesized by the solid phase synthesis method, insoluble resins known in the art are used. Examples of such insoluble resins include chloromethyl resins, hydroxymethyl resins, benzhydrylamine resins, aminomethyl resins, p-benzyloxybenzylalcohol resins, 4-methylbenzhydrylamine resins, 4-oxymethylphenylacetamidomethyl resins, polyacrylamide resins, 4-(2',4'-dimethoxyphenyl-hydroxymethyl) phenoxy resins and 4-(2',4'-dimethoxyphenyl-Fmoc aminoethyl) phenoxy resins. Using some of these resins, protected amino acids are condensed in turn from the C-terminal side of the PACAP peptides or the partial peptides thereof by methods known in the art, and then all protective groups are eliminated by treating with hydrogen fluoride, trifluoromethanesulfonic acid or trifluoroacetic acid. Thus, the desired PACAP peptides or the partial peptides thereof can be synthesized. For condensation of the protected amino acids, various activating agents used for peptide synthesis can be employed.

Examples of such agents include carbodiimides such as N,N'-dicyclohexylcarbodiimide, N,N'-diisopropylcarbodiimide and N-ethyl-N'-(3- dimethylaminopropyl)carbodiimide. When activation is conducted with the activating agent, the otected amino acids are added to the resin together with a cemization inhibiting additive such as 1-hydroxybenzotriole (HOBt) or 3-hydroxy-4-oxo-3,4-dihydrobenzotriazine HOOBt), or the protected amino acids previously activated symmetric acid anhydrides or as HOBt or HOOBt esters can added to the resin. Solvents used for activation of the otected amino acids or condensation with the resins include N,N'- dimethylformamide, N-methylpyrrolidone, dichloromethane and mixtures thereof. The activated amino id derivatives are usually used 1.5 to 4 times in excess. As a result of a test using the ninhydrin reaction, when condensation is insufficient, the condensation reaction is repeated without elimination of the protective groups, whereby sufficient condensation can be carried out. If sufficient condensation cannot be obtained even by repetition of the reaction, unreacted amino acids can be acetylated by using acetic anhydride or acetylimidazole.

As N-protected amino acids, it is preferred that the α-amino groups are protected with Boc groups; the hydroxyl groups of serine and threonine with Bzl groups; the ω- carboxylic acid groups of glutamic acid and aspartic acid with OBzl groups or OcHex groups; the ε-amino group of lysine with a Z group or Cl-Z group; the hydroxyl group of tyrosine with a Bzl, a Br-Z group or Cl$_2$-Bzl group; the guanido group of arginine with a Tos group, an Mts group or an NO$_2$ group; and the imidazole group of histidine with a Tos group, a DNP group or a Bom group. Further, the α-amino groups may also be protected with Fmoc groups; the hydroxyl groups of serine and threonine with Bu groups; the ω carboxyl of glutamic acid and aspartic acid with OBu groups; the ε-amino group of lysine with a Boc group, a Cl-Z group or a Z group; the hydroxyl group of tyrosine with a Bu group, Bzl group, a Br-Z group or a Cl$_2$-group; Bzl the quanido group of arginine with an Mtr group, a Trt group or a Z group; and the imidazole group of histidine with an Fmoc group, a Trt group or a Bum group, and finally a desired peptide can be obtained by treating the product with trifluoroacetic acid.

Examples of means for synthesis by the liquid phase method include the methods described in M. Bodanszky and M. A. Ondetti, *Peptide Synthesis*, Interscience Publishers, New (1966); Schroder and Lubke, *The peptide*, Academic Press, New York (1965); N. Izumiya et al., *Fundamentals and Experiments of Peptide Synthesis*, Maruzen (1985); and H. Yajima and S. Sakakibara, *Course of Biochemical Experiments* 1, *Chemistry of Proteins IV*, 205 (1977).

The 23 residues on the N-terminal side of the PACAP38 peptide are the smallest structure necessary for expression of c-AMP-producing activity, and the 24 to 26 residues also have activity similar to or higher than that of the above-mentioned 23 residues. Further, derivatives of which N-terminal amino acids are substituted for other amino acids such as Tyr, Phe and acetyl also have similar activity.

The new polypeptides of the present invention, like PACAP38 and PACAP27, are effective for the prevention of neuronal cell death which may be associated with a number of physiological conditions, such as AIDS infection, or mechanical damage to the brain. Therefore, they may be used as therapeutic agent for damage to neuronal cells. VIP, a peptide with significant homology to PACAP, is capable of protecting neurons from cell death induced by the gp120 envelope glycoprotein of the AIDS virus. Given the structural similarity between the present polypeptides and VIP, and the greater level of activity shown by the present polypeptides, it is expected that the present polypeptides will have a greater capacity for prevention of neuronal cell death. The present polypeptides completely prevented neuronal cell death by gp120 at low concentration of $10^{-14}$ to $10^{-7}$ M, preferably $10^{11}$ to $10^{-9}$ M.

The present polypeptides may be used as parenteral especially as injection or nebula. The pharmaceutical compositions can be prepared by incorporation of an effective amount of the peptide in combination with a pharmaceutically acceptable carrier such as physiological saline or a physiologically acceptable buffer at a concentration of 0.01 to 5% by weight, preferably 0.1 to 2% by weight. The preferable dose is 0.1 nmole/kg to 1 μg/kg, preferably 1 nmole/kg to 0.1 μg/kg per one administration, once to three times a day.

The present invention will be described in more detail with the following Examples. It is understood of course that these Examples are not intended to limit the scope of the invention.

EXAMPLE 1

Synthesis of PACAP-26-NH$_2$ (His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-NH$_2$)(SEQ ID NO: 3)

PACAP-26-NH$_2$ was synthesized by using 0.60 g (0.5 mmole) of a commercially available p-methyl BHA resin (Applied Biosystems Inc.) and a peptide synthesizer (Model 430A, Applied Biosystems Inc.).

A starting amino acid, Boc-Val, was activated with HOBt/DCC and then condensed to the resin. Thereafter, the Boc group on the resin was treated with 50% trifluoroacetic acid/methylene chloride to deprotect the amino group. The following protected amino acids were activated with HOBt/DCC and then condensed to this free amino group in turn according to the amino acid sequence of PACAP-26-NH$_2$:

Boc-Ala, Boc-Leu, Boc-Tyr(Br-Z), Boc-Lys(Cl-Z), Boc-Val, Boc-Met, Boc-Gln, Boc-Arg(Tos), Boc-Ser(Bzl), Boc-Gly, Boc-Asp(OcHex), Boc-Thr(Bzl), Boc-Phe, Boc-Ile and Boc-His(Bom)

After the same amino acid derivatives activated with DCC or HOBt/DCC were further condensed again, the unreacted amino groups were acetylated with acetic anhydride to obtain 1.54 g of a protected PACAP-26-NH$_2$ resin.

0.35 g of the resulting protected PACAP-26-NH2 resin was treated with 5 ml of anhydrous hydrogen fluoride in the presence of 0.60 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20,column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (2.6 X 7 cm) and eluted by a linear gradient of 0.1% aqueous trifluoroacetic acid and 50% acetonitrile containing 0.1% trifluoroacetic acid. The main fractions were combined and subjected to a YMC-ODS column (2.6×7 cm) again, followed by elution by a linear gradient of from 15% to 40% aqueous acetonitrile containing 0.1% trifluoroacetic acid. Then, the main fractions were collected and lyophilized. The resulting product was dissolved in 20 ml of 0.05 M aqueous ammonium acetate. The solution thus obtained was subjected to a CM-Cellulofine resin column (1×6 cm) and eluted by a linear gradient of from 0.05 M to 0.33 M aqueous ammonium acetate. The main fractions were combined, followed by lyophilization. 20 mg of a white powder was obtained as an acetate.

Anal. for amino acids: Asp 1.98(2), Thr 0.93(1), Ser 2.48(3), Glu 1.04(1), Gly 0.99(1), Ala 3.09(3), Val 1.95(2), Met 0.95(1), Ile 0.95(1), Leu 1.00(1), Tyr 3.03(3), Phe 0.99(1), Lys 2.96(3), His 1.00(1), Arg 2.19(2)

(M+N)$^+$ by mass spectrography: 3033.6

HPLC elution time: 19.52 minutes

Column conditions: Column: YMC-ODS (AM-301, S-5 120A) (4.6×100); Eluents: A (0.1% aqueous trifluoroacetic acid.); B (acetonitrile containing 0.1% trifluoroacetic acid); A linear gradient elution from eluent A to eluent B for 50 minutes; Flow rate: 1.0 ml/minute.

EXAMPLE 2

Synthesis of PACAP-26-OH (H-is-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-OH) (SEQ ID NO: 3)

PACAP-26-OH was synthesized by using 0.60 g (0.5 mmole) commercially available Boc-Val-OCH$_2$-PAM resin (Applied Biosystems Inc.) and a peptide synthesizer (Model 430A, ed Biosystems Inc.).

The Boc group on the resin was treated with 50% trifluoroacetic acid/methylene chloride to deprotect the amino group. Then, the following protected amino acids were activated with HOBt/DCC and each condensed in an amount of 2 mmoles to this free amino group in turn according to the amino acid sequence of PACAP-26:

Boc-Lys(Cl-Z), Boc-Arg(Tos), Boc-Gln, Boc-Tyr(Br-Z), Boc-Gly, Boc-Leu, Boc-Ala, Boc-Met, Boc-Ser(Bzl), Boc-Asp(OBzl), Boc-Thr(Bzl), Boc-Phe, Boc-Ile and Boc-His(Tos)

After the same amino acid derivatives activated with DCC or HOBt/DCC were further condensed again, the unreacted amino groups were acetylated with acetic anhydride to obtain 1.25 g of a protected PACAP-26-OCH2-PAM resin.

0.65 g of the resulting protected PACAP-26-OCH$_2$-PAM resin was treated with 6 ml of anhydrous hydrogen fluoride in the presence of 1.0 g of p-cresol at 0° C. 60 minutes, followed by removal of excess hydrogen fluoride by distillation under reduced pressure The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure The concentrated solution was applied on a Sephadex LH-20 column (2×75 cm) for elution acetic acid. The main fractions were collected, wed by removal by distillation under reduced pressure. Then, the residue was dissolved in 100 ml of 0.1% aqueous trifluoroacetic acid. The resulting solution was subjected to a YMC-ODS AM120 S-50 resin column (2.6×7 cm) and eluted by a linear gradient of 0.1% aqueous trifluoroacetic acid and 50% acetonitrile containing 0.1% trifluoroacetic acid. The main fractions were combined and lyophilized to obtain 90 mg of a white powder. This powder was dissolved and the resulting solution was subjected to a YMC-ODS column (2.6×7 cm) again, followed by elution by a linear gradient of from 15% to 40% aqueous acetonitrile containing 0.1% trifluoroacetic acid. Then, the fractions of 25% to 28% acetonitrile were collected and lyophilized. The resulting product was dissolved in 20 ml of 0.05 M aqueous ammonium acetate. The solution thus obtained was subjected to a CM-Cellulofine resin column (1×6 cm) and eluted by a linear gradient of from 0.05 M to 0.33 M aqueous ammonium acetate The main fractions were combined, followed by lyophilization. 20 mg of a white powder was obtained as an acetate.

Anal. for amino acids:
Asp 2.03(1), Thr 0.96(1), Ser 2.66(3), Glu 1.08(1), Gly 1.01(1), Ala 3.05(3), Val 1.98(2), Met 0.94(1), Ile 0.94(1), Leu 1.00(1), Tyr 2.96(3), Phe 0.95(1), Lys 2.99(3), His 1.03(1), Arg 2.25(2)
$(M+N)^+$ by mass spectrography: 3034.7
HPLC elution time: 18.68 minutes
Column conditions: Column: YMC-ODS (AM-301, S-5 120A) (4.6×100); Eluents: A (0.1% aqueous trifluoroacetic acid.), B (acetonitrile containing 0.1% trifluoroacetic acid); A linear gradient elution from eluent A to eluent B for 50 minutes; Flow rate: 1.0 ml/minute.

EXAMPLE 3

Synthesis of PACAP-24-NH$_2$ (His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-NH$_2$) (SEQ ID NO: 4)

PACAP-24-NH$_2$ was synthesized by using 0.61 g (0.5 mmole) of a commercially available p-methyl BHA resin (Applied Biosystems Inc.) and a peptide synthesizer (Model 430A, Applied Biosystems Inc.).

A starting amino acid, Boc-Ala, was activated with HOBt/DCC and then condensed to the resin. Thereafter, the Boc group on the resin was treated with 50% trifluoroacetic acid/methylene chloride to deprotect the amino group. The following protected amino acids were activated with HOBt/DCC and then condensed to this free amino group in turn according to the amino acid sequence of PACAP-24-NH$_2$:

Boc-Leu, Boc-Tyr(Br-Z), Boc-Lys(Cl-Z), Boc-Val, Boc-Ala, Boc-Met, Boc-Gln, Boc-Arg(Tos), Boc-Ser(Bzl), Boc-Gly, Boc-Asp(OcHex), Boc-Thr(Bzl), Boc-Phe, Boc-Ile and Boc-His(Bom)

After the same amino acid derivatives activated with DCC or HOBt/DCC were further condensed again, the unreacted amino groups were acetylated with acetic anhydride to obtain 2.31 g of a protected PACAP-24-NH$_2$ resin.

0.32 g of the resulting protected PACAP-24-NH$_2$ resin was treated with 5 ml of anhydrous hydrogen fluoride in the presence of 0.60 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (2.6×7 cm) and eluted by a linear gradient of 0.1% aqueous trifluoroacetic acid and 50% acetonitrile containing 0.1% trifluoroacetic acid. The main fractions were combined and subjected to a YMC-ODS column (2.6×7 cm) again, followed by elution by a linear gradient of from 15% to 35% aqueous acetonitrile containing 0.1% trifluoroacetic acid. Then, the main fractions were collected and lyophilized. The resulting product was dissolved in 20 ml of 0.05 M aqueous ammonium acetate. The solution thus obtained was subjected to a CM-Cellulofine resin column (1×6 cm) and eluted by a linear gradient of from water to 0.33 M aqueous ammonium acetate. The main fractions (0.18 to 0.22 M) were combined, followed by lyophilization. 12 mg of a white powder was obtained as an acetate.

Anal. for amino acids:
Asp 2.00(2), Thr 0.94(1), Ser 2.59(3), Glu 1.04(1), Gly 0.96(1), Ala 2.05(2), Val 0.95(1), Met 0.98(1), Ile 0.87(1), Leu 1.00(1), Tyr 2.85(3), Phe 0.90(1), Lys 2.92(3), His 0.99(1), Arg 2.19(2)
$(M+N)^+$ by mass spectrography: 2863.7
HPLC elution time: 17.39 minutes
Column conditions:
Column: YMC-ODS (AM-301, S-5 120A) (4.6×100);
Eluents: A (0.1% aqueous trifluoroacetic acid.),
B (acetonitrile containing 0.1%
trifluoroacetic acid)
A linear gradient elution from eluent A to eluent B for
50 minutes;
Flow rate: 1.0 ml/minute.

EXAMPLE 4

Synthesis of
PACAP-23-NH2(His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-NH$_2$)(SEQ ID NO: 5)

PACAP-23-NH$_2$ was synthesized by using 0.60 g (0.5 mmole) of a commercially available p-methyl BHA resin (Applied Biosystems Inc.) and a peptide synthesizer (Model 430A, Applied Biosystems Inc.).

A starting amino acid, Boc-Leu, was activated with HOBt/DCC and then condensed to the resin. Thereafter, the Boc group on the resin was treated with 50% trifluoroacetic acid/methylene chloride to deprotect the amino group. The following protected amino acids were activated with HOBt/DCC and condensed to this free amino group in turn according to the amino acid sequence of PACAP-23-NH$_2$:

Boc-Tyr(Br-Z), Boc-Lys(Cl-Z), Boc-Val, Boc-Ala, Boc-Met, Boc-Gln, Boc-Arg(Tos), Boc-Ser(Bzl), Boc-Gly, Boc-Asp(OcHex), Boc-Thr(Bzl), Boc-Phe, Boc-Ile and Boc-His(Bom)

After the same amino acid derivatives activated with DCC or HOBt/DCC were further condensed again, the unreacted amino groups were acetylated with acetic anhydride to obtain 2.31 g of a protected PACAP-23-NH$_2$ resin.

0.35 g of the resulting protected PACAP-23-NH$_2$ resin was treated with 5 ml of anhydrous hydrogen fluoride in the presence of 0.6 g of p-cresol at 0° C. for 60 minutes, followed by removal of excess hydrogen fluoride by distillation under reduced pressure The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (2.6×7 cm) and eluted by a linear gradient of 0.1% aqueous trifluoroacetic acid and 50% acetonitrile containing 0.1% trifluoroacetic acid. The main fractions were combined and subjected to a YMC-ODS column (2.6×7 cm) again, followed by elution by a linear gradient of from 15% to 30% aqueous acetonitrile containing 0.1% trifluoroacetic acid. Then, the main fractions of acetonitrile were collected and lyophilized. The resulting product was dissolved in 20 ml of 0.05 M aqueous ammonium acetate. The solution thus obtained was subjected to a CM-Cellulofine resin column (1×6 cm) and eluted by a linear gradient of from water to 0.70 M aqueous ammonium acetate The main fractions were combined, followed by lyophilization. 10 mg of a white powder was obtained as an acetate.

Anal. for amino acids:
Asp 1.98(2), Thr 0.95(1), Ser 2.53(3), Glu 1.07(1), Gly 1.01(1), Ala 1.07(1), Val 0.96(1), Met 0.95(1), Ile 0.91(1), Leu 2.00(2), Tyr 2.99(3), Phe 0.94(1), Lys 2.88(3), His 0.97(1), Arg 1.96(2)
$(M+N)^+$ by mass spectrography: 2792.9
HPLC elution time: 17.48 minutes
Column conditions:
Column: YMC-ODS (AM-301, S-5 120A) (4.6×100);
Eluents: A (0.1% aqueous trifluoroacetic acid.),
B (acetonitrile containing 0.1%
trifluoroacetic acid);
A linear gradient elution from eluent A to eluent B for
50 minutes;
Flow rate: 1.0 ml/minute.

EXAMPLE 5

Synthesis of PACAP-23-OH (His-Ser-Asp-Gly-Ile-Phe-Thr-p-Ser-Tyr-Ser-Arg-Tyr-Arg-Lys-Gln-Met-Ala-Val-Lys-Lys-Tyr-Leu-OH) (SEQ ID NO: 5)

PACAP-23-OH was synthesized by using 0.65 g (0.5 mmole) of a commercially available Boc-Leu-OCH$_2$-PAM resin (Applied Biosystems Inc.) and a peptide synthesizer (Model 430A, Applied Biolsystems Inc.).

The Boc group on the resin was treated with 50% trifluoroacetic acid/methylene chloride to deprotect the amino group. Then, the following protected amino acids were activated with HOBt/DCC and each condensed in an amount of 2 mmoles to this free amino group in turn according to the amino acid sequence of PACAP-23:

Boc-Tyr(Br-Z), Boc-Lys(Cl-Z), Boc-Val, Boc-Ala, Boc-Met, Boc-Gln, Boc-Arg(Tos), Boc-Ser(Bzl), Boc-Asp(OBzl), Boc-Thr(Bzl), Boc-Phe, Boc-Ile, Boc-Gly, and Boc-His(Dom)

After the same amino acid derivatives activated with DCC or HOBt/DCC were further condensed again, the unreacted amino groups were acetylated with acetic anhydride to obtain 2.50 g of a protected PACAP-23-OCH$_2$-PAM resin.

0.86 g of the resulting protected PACAP-23-OCH$_2$-PAM resin was treated with 10 ml of anhydrous hydrogen fluoride in the presence of 1.0 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (2.6×7 cm) and eluted by a linear gradient of 0.1% aqueous trifluoroacetic acid and 50% acetonitrile containing 0.1% trifluoroacetic acid. The main fractions were combined and lyophilized to obtain 90 mg of a white powder as an acetate.

Anal. for amino acids: Asp 1.96(2), Thr 0.88(1), Ser 2.13(3), Glu 1.07(1), Gly 0.98(1), Ala 1.00(1), Val 1.00(1), Met 0.89(1), Ile 0.94(1), Leu 0.98(1), Tyr 2.99(3), Phe 1.00(1), Lys 2.95(3), His 0.99(1), Arg 2.18(2)
$(M+N)^+$ by mass spectrography: 2793.5
HPLC elution time: 17.28 minutes
Column conditions;
Column: YMC-ODS (AM-301, S-5 120A) (4.6×100);
Eluents: A (0.1% aqueous trifluoroacetic acid.),
B (acetonitrile containing 0.1%
trifluoroacetic acid),
A linear gradient elution from eluent A to eluent B for
50 minutes;
Flow rate: 1.0 ml/minute.

EXAMPLE 6

Synthesis of Acetyl-PACAP-(2-26)-NH$_2$(Acetyl-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-NH$_2$(SEQ ID NO: 6)

Acetyl-PACAP-(2-26)-NH$_2$ was synthesized by using 0.60 g (0.5 mmole) of a commercially available p-methyl BHA resin (Applied Biosystems Inc.) and a peptide synthesizer (Model 430A, Applied Biosystems Inc.).

A starting amino acid, Boc-Val, was activated with HOBt/DCC and then condensed to the resin. Thereafter, the Boc group on the resin was treated with 50% trifluoroacetic acid/methylene chloride to deprotect the amino group. The following protected amino acids were activated with HOBt/DCC and then condensed to this free amino group in turn according to the amino acid sequence of PACAP-(2-26)-NH$_2$:

Boc-Ala, Boc-Leu, Boc-Tyr(Br-Z), Boc-Lys(Cl-Z), Boc-Val, Boc-Met, Boc-Gln, Boc-Arg(Tos), Boc-Ser(Blz), Boc-Gly, Boc-Asp(OcHex), Boc-Thr(Bzl), Boc-Phe and Boc-Ile The same amino acid derivatives activated with DCC or HOBt/DCC were further condensed again. After Boc-Ser(Bzl) was finally condensed, the Boc group was eliminated and then acetylated with acetic anhydride for protection to obtain 1.50 g of a protected acetyl-PACAP-26-NH$_2$ resin.

0.41 g of this resin was treated with 10 ml of anhydrous hydrogen fluoride in the presence of 0.8 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure The concentrated solution was applied on a Sephadex LH-20 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (2.6×7 cm) and eluted by a linear gradient of 0.1% aqueous trifluoroacetic acid. The main fractions were combined and subjected to a YMC-ODS column (2.6×7 cm) again, followed by elution by a linear gradient of from 15% to 35% aqueous acetonitrile containing 0.1% trifluoroacetic acid. Then, the fractions of 30% to 32% acetonitrile were collected and lyophilized. The resulting product was dissolved in 20 ml of 0.05 M aqueous ammonium acetate. The solution thus obtained was subjected to a CM-Cellulofine resin column (1×6 cm) and eluted by a linear gradient of from water to 0.33 M aqueous ammonium acetate. The main fractions (0.18 to 0.22 M) were combined, followed by lyophilization. 18 mg of a white powder was obtained as an acetate.

Anal. for amino acids:
Asp 1.96(2), Thr 0.94(1), Ser 2.57(3), Glu 1.07(1), Gly 0.95(1), Ala 3.00(3), Val 1.96(2), Met 0.88(1), Ile 0.88(1), Leu 0.98(1), Tyr 2.87(3), Phe 0.90(1), Lys 2.91(3), Arg 2.17(2)
(M+N)+ by mass spectrography: 3051.6
HPLC elution time: 20.40 minutes
Column conditions;
Column: YMC-ODS (AM-301, S-5 120A) (4.6×100);
Eluents: A (0.1% aqueous trifluoroacetic acid.),
B (acetonitrile containing 0.1%
trifluoroacetic acid);
A linear gradient elution from eluent A to eluent B for
50 minutes;
Flow rate: 1.0 ml/minute.

EXAMPLE 7

Synthesis of (Tyr1)PACAP-(2-24)-NH$_2$(Tyr-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-NH$_2$)(SEQ ID NO: 7)

(Tyr$^1$)PACAP-(2-24)-NH$_2$ was synthesized by using 0.61 g(0.5 mmole) of a commercially available p-methyl BHA resin (Applied Biosystems Inc.) and a peptide synthesizer (Model 430A, Applied Biosystems Inc.).

A starting amino acid, Boc-Ala, was activated with HOBt/DCC and then condensed to the resin. Thereafter, the Boc group on the resin was treated with 50% trifluoroacetic acid/methylene chloride to deprotect the amino group. The following protected amino acids were activated with HOBt/DCC and then condensed to this free amino group in turn according to the amino acid sequence of (Tyr$^1$)PACAP-(2-24)-NH$_2$.

Boc-Leu, Boc-Tyr(Br-Z), Boc-Lys(Cl-Z), Boc-Val, Boc-Ala, Boc-Met, Boc-Gln, Boc-Arg(Tos), Boc-Ser(Bzl), Boc-Gly, Boc-Asp(OcHex), Boc-Thr(Bzl), Boc-Phe and Boc-Ile After the same amino acid derivatives activated with DCC or HOBt/DCC were further condensed again, the unreacted amino groups were acetylated with acetic anhydride to obtain 2.20 g of a protected (Tyr$^1$)PACAP-24-NH$_2$ resin.

0.31 g of the (Tyr$^1$)PACAP-24-NH$_2$ resin was treated with 5 ml of anhydrous hydrogen fluoride in the presence of 0.53 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (2.6×7 cm) and eluted by a linear gradient of 0.1% aqueous trifluoroacetic acid and 50% acetonitrile containing 0.1% trifluoroacetic acid. The main fractions were combined and subjected to a YMC-ODS column (2.6×7 cm) again, followed by elution by a linear gradient of from 15% to 35% aqueous acetonitrile containing 0.1% trifluoroacetic acid. Then, the main fractions were collected and lyophilized. The resulting product was dissolved in 20 ml of 0.05 M aqueous ammonium acetate. The solution thus obtained was subjected to a CM-Cellulofine resin column (1×6 cm) and eluted by a linear gradient of from water to 0.33 M aqueous ammonium acetate. The main fractions were combined, followed by lyophilization. Thus, 15 mg of a white powder was obtained as an acetate.

Anal. for amino acids: Asp 1.99(2), Thr 0.95(1), Ser 2.54(3), Glu 1.07(1), Gly 1.02(1), Ala 2.01(2), Val 0.99(1), Met 0.99(1), Ile 0.93(1), Leu 1.00(1), Tyr 4.11(4), Phe 0.96(1), Lys 2.88(3), Arg 1.99(2)
(M+N)+ by mass spectrography: 2889.4
HPLC elution time: 18.76 minutes
Column conditions;
Column: WAKOSIL 5C18 (4.6×100);
Eluents: A (0.1% aqueous trifluoroacetic acid),
B (acetonitrile containing 0.1%
trifluoroacetic acid);
A linear gradient elution from eluent A to eluent B for
50 minutes;
Flow rate: 1.0 ml/minute.

EXAMPLE 8

Established cells derived from adrenal medullas, PC12h, were cultivated in Dulbecco's modified Eagle's medium containing 10% semi-fetal calf serum at 37° C. A 48-well collagen-treated plate was inoculated with $5 \times 10^4$ cells per well, and cultivation was conducted for 7 to 10 days. Then, the culture medium was exchanged for 500 μl of Hank's balanced salt solution, followed by standing at 37° C. for 30 minutes. A sample to be tested dissolved in the same solution was added thereto, and cultivation was conducted at 37° C. for 2 hours. Subsequently, the amount of c-AMP in this culture solution was assayed by using a kit for measuring c-AMP (Amersham Inc.). FIG. 1 shows the results assayed for VIP, the compounds of the present invention and PACAP20-OH (comparison: the compound which is composed of the 20 amino acids from the N-terminus of PACAP38 and whose C-terminus is carboxyl).

As apparent from FIG. 1, the PACAP derivatives of the present invention have c-AMP-producing activity. Compared therewith, VIP having a similar structure is weak in this activity, and for PACAP20-OH, such activity can not be observed.

The PACAP derivatives of the present invention are short in the length of chains, compared with PACAP38 and PACAP27, so that they can be easily synthesized. Further, PACAP38, PACAP27 and the compounds of the present invention are soluble in water. However, the derivatives of the present invention are more difficult to adhere to vessel walls than PACAP 38 and PACAP 27. In synthesizing and forming pharmaceutical preparations, therefore, the operations are easily carried out. Moreover, since the derivatives of the present invention are short in the length of chains, they are expected to be easily administered in the body.

EXAMPLE 9

Synthesis of PACAP-25-NH₂ (His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-NH₂(SEQ ID NO: 8)

PACAP-25-NH₂ was synthesized by using 0.60 g (0.5 mmole) of a commercially available p-methyl BHA resin (Applied Biosystems Inc.) and a peptide synthesizer (Model 430A, Applied Biosystems Inc.).

A starting amino acid, Boc-Ala, was activated with HOBt/DCC and then condensed to the resin. Thereafter, the Boc group on the resin was treated with 50% trifluoroacetic acid/methylene chloride to deprotect the amino group. The following protected amino acids were activated with HOBt/DCC and then condensed to this free amino group in turn according to the amino acid sequence of PACAP-26-NH₂:

Boc-Ala, Boc-Leu, Boc-Tyr(Br-Z), Boc-Lys(Cl-Z), Boc-Val, Boc-Met, Boc-Gln, Boc-Arg(Tos), Boc-Ser(Bzl), Boc-Gly, Boc-Asp(OcHex), Boc-Thr(Bzl), Boc-Phe, Boc-Ile and Boc-His(Bom)

After the same amino acid derivatives activated with DCC or HOBt/DCC were further condensed again, the unreacted amino groups were acetylated with acetic anhydride to obtain 1.50 g of a protected PACAP-25-NH₂ resin.

0.35 g of the resulting protected PACAP-25-NH₂ resin was treated with 5 ml of anhydrous hydrogen fluoride in the presence of 0.60 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (2.6×7 cm) and eluted by a linear gradient of 0.1% aqueous trifluoroacetic acid and 50% acetonitrile containing 0.1% trifluoroacetic acid. The main fractions were combined and subjected to a YMC-ODS column (2.6×7 cm) again, followed by elution by a linear gradient of from 15% to 40% aqueous acetonitrile containing 0.1% trifluoroacetic acid. Then, the main fractions were collected and lyophilized. The resulting product was dissolved in 20 ml of 0.05 M aqueous ammonium acetate. The solution thus obtained was subjected to a CM-Cellulofine resin column (1×6 cm) and eluted by a linear gradient of from 0.05 M to 0.33 M aqueous ammonium acetate. The main fractions were combined, followed by lyophilization. 20 mg of a white powder was obtained as an acetate.

Anal. for amino acids:
Asp 1.95(2), Thr 0.95(1), Ser 2.71(3), Glu 1.04(1), Gly 0.99(1), Ala 3.09(3), Val 0.90(1), Met 0.95(1), Ile 0.95(1), Leu 1.00(1), Tyr 3.10(3), Phe 0.99(1), Lys 2.96(3), His 1.05(1), Arg 2.19(2)

$(M+N)^+$ by mass spectrography: 2934.5

HPLC elution time: 18.21 minutes

Column conditions;

Column: YMC-ODS (AM-301, S-5 120A) (4.6×100);

Eluents: A (0.1% aqueous trifluoroacetic acid.),
B (acetonitrile containing 0.1% trifluoroacetic acid);

A linear gradient elution from eluent A to eluent B for 50 minutes;

Flow rate: 1.0 ml/minute.

The following references, which are referred to for their disclosures at various points in this application, are incorporated herein by reference.

Peptide Synthesis, Interscience Publishers, New York (1966)

The peptide, Academic Press, New York (1965)

Fundamentals and Experiments of Peptide Synthesis, Maruzen (1985)

Course of Biochemical Experiments 1, Chemistry of Proteins IV, 205 (1977).

---

What is claimed is:

1. A polypeptide represented by the following general formula or a pharmaceutically acceptable salt thereof:

X-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Y(X-SEQ ID NO:2-Y)

wherein X represents an aromatic amino acid residue or a carboxylic acid-derived acyl group, and Y represents $NH_2$, OH, Ala-$NH_2$, Ala-OH, Ala-Ala-$NH_2$, Ala-Ala-OH, Ala-Ala-Val-$NH_2$ or Ala-Ala-Val-OH.

2. A polypeptide or a pharmaceutically acceptable salt thereof claimed in claim 1, in which X is an aromatic amino acid residue.

3. A polypeptide or a pharmaceutically acceptable salt thereof claimed in claim 2, in which said aromatic amino acid is His, Tyr, Phe or Trp.

4. A polypeptide or a pharmaceutically acceptable salt thereof claimed in claim 1, in which X is a carboxylic acid-derived acyl group.

5. A polypeptide or a pharmaceutically acceptable salt thereof claimed in claim 4, in which X is a carboxylic acid-derived acyl group having 1 to 8 carbon atoms.

6. A polypeptide or a pharmaceutically acceptable salt thereof claimed in claim 5, in which X is an acetyl group.

7. A polypeptide or a pharmaceutically acceptable salt thereof claimed in claim 1, in which X is His and Y is Ala-Ala-Val-NH$_2$.

8. A polypeptide or a pharmaceutically acceptable salt thereof claimed in claim 1, in which X is His and Y is Ala-Ala-Val-OH.

9. A polypeptide or a pharmaceutically acceptable salt thereof claimed in claim 1, in which X is His and Y is Ala-NH$_2$.

10. A polypeptide or a pharmaceutically acceptable salt thereof claimed in claim 1, in which X is His and Y is NH$_2$.

11. A polypeptide or a pharmaceutically acceptable salt thereof claimed in claim 1, in which X is His and Y is OH.

12. A polypeptide or a pharmaceutically acceptable salt thereof claimed in claim 1, in which X is acetyl and Y is Ala-Ala-Val-NH$_2$.

13. A polypeptide or a pharmaceutically acceptable salt thereof claimed in claim 1, in which X is Tyr and Y is Ala-NH$_2$.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:1:

```
His Ser Asp Gly Ile Phe Thr Asp Ser Tyr Ser Arg Tyr Arg Lys Gln
 1               5                   10                  15
Met Ala Val Lys Lys Tyr Leu Ala Ala Val Leu Gly Lys Arg Tyr Lys
            20                  25                  30
Gln Arg Val Lys Asn Lys
            35
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

```
Ser Asp Gly Ile Phe Thr Asp Ser Tyr Ser Arg Tyr Arg Lys Gln Met
 1               5                   10                  15
Ala Val Lys Lys Tyr Leu
            20
```

( 2 ) INFORMATION FOR SEQ ID NO:3:

( i ) SEQUENCE CHARACTERISTICS:
        ( A ) LENGTH: 26 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:3:

```
His Ser Asp Gly Ile Phe Thr Asp Ser Tyr Ser Arg Tyr Arg Lys Gln
 1               5                   10                  15
Met Ala Val Lys Lys Tyr Leu Ala Ala Val
            20                  25
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:4:

```
His Ser Asp Gly Ile Phe Thr Asp Ser Tyr Ser Arg Tyr Arg Lys Gln
 1               5                   10                  15
Met Ala Val Lys Lys Tyr Leu Ala
            20
```

( 2 ) INFORMATION FOR SEQ ID NO:5:

( i ) SEQUENCE CHARACTERISTICS:
        ( A ) LENGTH: 23 amino acids
        ( B ) TYPE: amino acid (D) TOPOLOGY: linear (ii) MOLECULE TYPE: peptide (xi) SEQUENCE DESCRIPTION: SEQ ID NO:5:

His Ser Asp Gly Ile Phe Thr Asp Ser Tyr Ser Arg Tyr Arg Lys Gln
1               5                   10                  15

Met Ala Val Lys Lys Tyr Leu
            20

(2) INFORMATION FOR SEQ ID NO:6:

(i) SEQUENCE CHARACTERISTICS:
    (A) LENGTH: 25 amino acids
    (B) TYPE: amino acid
    (D) TOPOLOGY: linear (ii) MOLECULE TYPE: peptide (xi) SEQUENCE DESCRIPTION: SEQ ID NO:6:

Ser Asp Gly Ile Phe Thr Asp Ser Tyr Ser Arg Tyr Arg Lys Gln Met
1               5                   10                  15

Ala Val Lys Lys Tyr Leu Ala Ala Val
            20                  25

(2) INFORMATION FOR SEQ ID NO:7:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (xi) SEQUENCE DESCRIPTION: SEQ ID NO:7:

Tyr Ser Asp Gly Ile Phe Thr Asp Ser Tyr Ser Arg Tyr Arg Lys Gln
1               5                   10                  15

Met Ala Val Lys Lys Tyr Leu Ala
            20

(2) INFORMATION FOR SEQ ID NO:8:

(i) SEQUENCE CHARACTERISTICS:
    (A) LENGTH: 25 amino acids
    (B) TYPE: amino acid
    (D) TOPOLOGY: linear (ii) MOLECULE TYPE: peptide (xi) SEQUENCE DESCRIPTION: SEQ ID NO:8:

His Ser Asp Gly Ile Phe Thr Asp Ser Tyr Ser Arg Tyr Arg Lys Gln
1               5                   10                  15

Met Ala Val Lys Lys Tyr Leu Ala Ala
            20                  25